US008557177B1

(12) United States Patent
Elrod

(10) Patent No.: US 8,557,177 B1
(45) Date of Patent: *Oct. 15, 2013

(54) METHOD OF DESCENTING HUNTER'S CLOTHING

(75) Inventor: Scott Elrod, Angleton, TX (US)

(73) Assignee: Parah, LLC, Angleton, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/099,270

(22) Filed: May 2, 2011

Related U.S. Application Data

(63) Continuation of application No. 11/018,620, filed on Dec. 21, 2004, now Pat. No. 7,939,015.

(51) Int. Cl.
A61L 9/00 (2006.01)
A61L 2/00 (2006.01)
A61L 2/18 (2006.01)
A62B 7/08 (2006.01)

(52) U.S. Cl.
USPC ................... 422/5; 422/28; 422/29; 422/120; 422/123

(58) Field of Classification Search
USPC .................................. 422/5, 28, 29, 120, 123
See application file for complete search history.

(56) References Cited

U.S. PATENT DOCUMENTS

| 1,961,878 | A | 6/1934 | Gilkey |
| 2,203,188 | A | 6/1940 | Beer |
| 3,214,364 | A | 10/1965 | Van Tuyle et al. |
| 3,421,836 | A | 1/1969 | Sundin et al. |
| 3,601,292 | A | 8/1971 | Bliss |
| 3,670,425 | A | 6/1972 | Benjamin |
| 3,750,556 | A | 8/1973 | Duke et al. |
| 3,937,967 | A | 2/1976 | Steinitz |
| 3,949,056 | A | 4/1976 | Nakshbendi |
| 4,045,316 | A | 8/1977 | Legan |
| 4,238,857 | A | 12/1980 | Waters |
| 4,309,388 | A | 1/1982 | Tenney et al. |
| 4,374,571 | A | 2/1983 | Hirvela |
| 4,735,010 | A | 4/1988 | Grinarml |
| 4,811,159 | A | 3/1989 | Foster, Jr. |
| 4,863,687 | A | 9/1989 | Stevens et al. |
| 4,867,052 | A | 9/1989 | Cipelletti |
| 4,904,289 | A | 2/1990 | Miyakami et al. |
| 4,941,270 | A | 7/1990 | Hoffman |
| 4,953,674 | A | 9/1990 | Landes |
| 4,990,311 | A | 2/1991 | Hirai et al. |
| 5,087,426 | A | 2/1992 | Inoue et al. |
| 5,152,077 | A | 10/1992 | Liang |
| 5,185,129 | A | 2/1993 | Koutrakis et al. |
| 5,192,500 | A | 3/1993 | Treddenick |
| 5,303,496 | A | 4/1994 | Kowalkowski |
| 5,316,182 | A | 5/1994 | Lee et al. |
| 5,342,415 | A | 8/1994 | Wasinger et al. |
| 5,383,236 | A | 1/1995 | Sesselmann |
| 5,429,271 | A | 7/1995 | Porter |
| 5,433,230 | A | 7/1995 | Miller |
| 5,433,919 | A | 7/1995 | Baltes |
| 5,457,054 | A | 10/1995 | Geisinger et al. |
| 5,468,454 | A | 11/1995 | Kim |
| 5,484,472 | A | 1/1996 | Weinberg |
| 5,514,345 | A | 5/1996 | Garbutt et al. |
| 5,520,893 | A | 5/1996 | Kasting, Jr. et al. |
| 5,539,930 | A | 7/1996 | Sesselmann |
| 5,547,476 | A | 8/1996 | Siklosi et al. |
| 5,667,564 | A | 9/1997 | Weinberg |
| 5,681,355 | A | 10/1997 | Davis et al. |
| 5,762,648 | A | 6/1998 | Yeazell |
| 5,766,560 | A | 6/1998 | Cole |
| 5,789,368 | A | 8/1998 | You et al. |
| 5,790,987 | A | 8/1998 | Sesselmann |
| 5,795,544 | A | 8/1998 | Matz |
| 5,829,066 | A | 11/1998 | Aibe |
| 5,833,740 | A | 11/1998 | Brais |
| 5,835,840 | A | 11/1998 | Goswami |
| 5,891,391 | A | 4/1999 | Fore |
| 5,911,957 | A | 6/1999 | Khatchatrian et al. |
| 5,931,014 | A | 8/1999 | Cole |
| 5,942,438 | A | 8/1999 | Antonoplos et al. |
| 5,983,834 | A | 11/1999 | Tai |
| 6,007,770 | A | 12/1999 | Peiper et al. |
| 6,009,559 | A | 1/2000 | Sesselmann |

(Continued)

FOREIGN PATENT DOCUMENTS

| EP | 0261987 | 3/1988 |
| JP | 06-327749 | 11/1994 |

(Continued)

OTHER PUBLICATIONS

Bomms Terminator. Game Finder—Outdoor Enhancement Systems, Web page print outs from http://www.game-finder.com/bomms-terminator.aspx, printed on Dec. 23, 2006 (2 pages).

(Continued)

Primary Examiner — Regina M. Yoo
(74) Attorney, Agent, or Firm — Holland & Hart LLP

(57) ABSTRACT

A method for removing the human scent and any other scent that is not advantageous to the environment you are in from clothing and equipment used by sportsmen by the use of gaseous ozone or hydroxyl and hydroperoxide ions. The gas is applied directly or indirectly to the clothing, equipment and body while the hunter is in the field and/or prior to or after the hunt. The method can also be used by fishermen to eliminate fish odor. The method of delivering a gas in compressed/generated form from a container.

20 Claims, No Drawings

(56) References Cited

U.S. PATENT DOCUMENTS

| | | |
|---|---|---|
| 6,074,608 A | 6/2000 | Matz |
| 6,094,549 A | 7/2000 | Hiraoka et al. |
| 6,134,718 A | 10/2000 | Sesselmann |
| 6,134,806 A | 10/2000 | Dhaemers |
| 6,149,038 A | 11/2000 | Tsai |
| 6,153,111 A | 11/2000 | Conrad et al. |
| 6,156,268 A | 12/2000 | Curry et al. |
| 6,163,098 A | 12/2000 | Taylor et al. |
| 6,182,671 B1 | 2/2001 | Taylor et al. |
| 6,218,189 B1 | 4/2001 | Antonoplos et al. |
| 6,267,242 B1 | 7/2001 | Nagata et al. |
| 6,284,204 B1 | 9/2001 | Cole et al. |
| 6,312,507 B1 | 11/2001 | Taylor et al. |
| 6,336,964 B1 | 1/2002 | Omatsu et al. |
| 6,340,447 B2 | 1/2002 | Johnson |
| 6,340,497 B2 | 1/2002 | Wilson |
| 6,355,216 B1 | 3/2002 | Kristiansson et al. |
| 6,368,867 B1 | 4/2002 | Gibson et al. |
| 6,379,435 B1 | 4/2002 | Fukunaga et al. |
| 6,503,547 B1 | 1/2003 | Lima |
| 6,564,591 B2 | 5/2003 | Noyes |
| 6,565,805 B2 | 5/2003 | Khatchatrian et al. |
| 6,576,190 B1 | 6/2003 | Park |
| 6,613,277 B1 | 9/2003 | Monagan |
| 6,630,105 B1 | 10/2003 | O'Neill et al. |
| 6,632,407 B1 | 10/2003 | Lau et al. |
| 6,635,439 B1 | 10/2003 | Morrison et al. |
| 6,679,419 B1 | 1/2004 | Sarracino |
| D486,357 S | 2/2004 | Leba et al. |
| 6,790,411 B1 | 9/2004 | Read |
| 6,896,853 B2 | 5/2005 | Lau et al. |
| 6,967,008 B1 | 11/2005 | Barnes |
| 7,117,687 B2 | 10/2006 | Naaman |
| 7,118,608 B2 | 10/2006 | Lovell |
| 7,186,373 B2 | 3/2007 | Centanni |
| 7,222,634 B2 | 5/2007 | Hess et al. |
| 7,662,636 B2 | 2/2010 | Maruo et al. |
| 7,939,015 B1 * | 5/2011 | Elrod ................ 422/5 |
| 2002/0030022 A1 | 3/2002 | Bradley |
| 2002/0071795 A1 | 6/2002 | Jensen |
| 2002/0094298 A1 | 7/2002 | Monagan |
| 2003/0044308 A1 | 3/2003 | Toth |
| 2003/0066767 A1 | 4/2003 | Felsenthal |
| 2003/0089010 A1 | 5/2003 | Wechter et al. |
| 2003/0108460 A1 | 6/2003 | Andreev et al. |
| 2003/0111435 A1 | 6/2003 | Chen |
| 2004/0002349 A1 | 1/2004 | Yamagishi et al. |
| 2004/0047775 A1 | 3/2004 | Lau et al. |
| 2004/0096354 A1 | 5/2004 | Normura et al. |
| 2004/0149329 A1 | 8/2004 | Hess et al. |
| 2004/0163184 A1 | 8/2004 | Waldron et al. |
| 2004/0221396 A1 | 11/2004 | Johnson |
| 2005/0186108 A1 | 8/2005 | Fields |
| 2005/0207951 A1 | 9/2005 | Lee et al. |
| 2006/0006122 A1 | 1/2006 | Burns et al. |
| 2006/0096331 A1 | 5/2006 | Kim |
| 2006/0151896 A1 | 7/2006 | Wang |
| 2006/0266221 A1 * | 11/2006 | Fink et al. ................ 96/224 |
| 2007/0092414 A1 | 4/2007 | Malyon |
| 2007/0166186 A1 | 7/2007 | Stec |
| 2007/0212253 A1 | 9/2007 | Elrod |
| 2008/0036594 A1 | 2/2008 | Kates |
| 2009/0038555 A1 | 2/2009 | Reese |
| 2009/0139459 A1 | 6/2009 | Habacivch et al. |
| 2010/0071633 A1 | 3/2010 | Elrod |
| 2010/0107991 A1 | 5/2010 | Elrod |
| 2010/0289655 A1 | 11/2010 | Elrod et al. |

FOREIGN PATENT DOCUMENTS

| | | |
|---|---|---|
| JP | 08-168363 A | 7/1996 |
| JP | 09239018 A | 9/1997 |
| JP | 09262141 A | 10/1997 |
| JP | 1109948 A | 1/1999 |
| JP | 11009949 A | 1/1999 |
| JP | 11226106 A | 8/1999 |
| JP | 11226108 A | 8/1999 |
| JP | 2002345937 A | 12/2002 |
| JP | 2003001237 A | 1/2003 |
| JP | 2003024426 A | 1/2003 |
| WO | 01/51096 | 7/2001 |
| WO | 0177283 A1 | 10/2001 |
| WO | 03/089017 | 10/2003 |
| WO | 2004/067043 | 8/2004 |
| WO | 2005/021135 | 3/2005 |
| WO | 2005/077425 | 8/2005 |

OTHER PUBLICATIONS

Fehrenbacher, Jill, Robotic Pollution-Sniffing Eco Dogs! [on-line], Feb. 26, 2007; retrieved from the internet: URL: http://inhabitat.com/robotic-pollution-sniffing-eco-dogs/.

Terminator 800, Game Finder, Feb. 13, 2003.

U.S. Appl. No. 60/543,505, filed Feb. 11, 2004 (1 page).

Detection of the cyanobaterial hepatoxins microsystins; in toxicology & Applied Pharmacology, McElhiney et al., Dec. 2003 (pp. 219-230).

BOMMS Terminator, Game Finder, May 24, 2002.

Machine Language translation for JP 08-1638363A, pub. Jul. 1996.

English language abstract for JP 2002345937 A, pub. Dec. 2002.

* cited by examiner

METHOD OF DESCENTING HUNTER'S CLOTHING

RELATED APPLICATION

This is a continuation of U.S. patent application Ser. No. 11/018,620, filed on 21 Dec. 2004, now U.S. Pat. No. 7,939,015, the disclosure of which is incorporated, in its entirety, by this reference.

FIELD OF THE INVENTION

The invention relates to a method of de-scenting the clothes and apparatus of sportsmen, both professional, non professional, bikers, campers and the like. More particularly, there is provided a method of removing human scent and any other scent that is not advantageous in that environment from clothing and equipment of hunters and fish odors from fisherman utilizing an oxidizing agent which is ozone or a combination of hydroxyl and hydroperoxide ions.

BACKGROUND OF THE INVENTION

Animals have an acute sense of smell and are capable of recognizing a human scent or any other scent that is not advantageous in that environment at long distances. To avoid such recognition a hunter will attempt to stay down wind of the animal being hunted. The more common method used by hunters to trick the animals is to mask the human odor utilizing an animal scent. Unfortunately the animal scents which are utilized, are obnoxious and linger on the clothing for long periods of time. Some of the scents utilized include animal urine. A hunter who is camping overnight does not desire the animal scents to be carried over to bedtime, home, car, etc.

There are other drawbacks in utilizing animal scents or any other scents. The scent may attract a predator of the game which the hunter is not hunting for which the hunter may not be prepared to encounter. Descenting packs or containers containing food or any other substance that contains scents that may not be natural to the given environment. Also, the weapon used by the hunter has an odor recognizable by some animals which cannot be disguised with a scent.

Fishermen have the problem of fish odor on their hands and clothes which is difficult to remove. For fishermen camping overnight the fish odor is not only undesirable because of the odor but can also attract animals such as bears which the fishermen is not prepared to meet.

Hunters have prepared their clothing before hand by washing to remove prior scents and/or human odor. The washing materials may also leave an odor. However, out in the field the hunter can sweat and permeate the clothing with a human scent. It would be desirable to deodorize clothing during a hunt or while on a fishing trip.

Ozone has been used for decontaminating buildings and for deodorizing denim garment. U.S. Pat. No. 5,833,740 to Brais discloses an apparatus for sterilizing bottles utilizing ozone. The reference recognizes that ozone in large quantities can be harmful or irritating. Consequently, it was necessary to provide means for decomposing the excess ozone and/or to cause its escape into the atmosphere.

Ozone is a powerful oxidizing agent. Ozone has 150% of the oxidizing potential of chlorine and twice the oxidizing potential of bromine. Ozone has been shown to be much more effective than chlorine with a reaction time up to 10 times faster. Ozone also readily self-destructs into simple diatomic oxygen due to its inherent instability. Ozone oxidizes biological products and kills bacteria.

Catalytic ionization using ultraviolet light is known to produce a mixture of hydroxyl and hydroperoxide ions. Ionization devices which are used in automobiles to eliminate smoke and odors are known in the art to product hydroxyl and hydroperoxide ions.

SUMMARY OF THE INVENTION

The invention relates to a method for deodorizing the clothing apparatus of sportsmen, professional or non professional. More particularly, there is provided a method for removing human scent or any other foreign scent of clothing used by hunters before or during a hunt through the use of ozone or hydroxyl and hydroperoxide ions produced by ionization in a manner that would not cause irritation or injury to the user or equipment. Also, there is provided a method for removing fish odor from fishermen and their clothing and equipment while in the field, including lures, tackle boxes and containers. The principal objective of the invention is the provision of a method for effectively removing human scent from clothing used by sportsmen.

It is another object of the invention to deodorize fish odor on fishermen.

It is yet another object of the invention to de-scent or deodorize sportsmen while out in the field by the use of ozone or hydroxyl and hydroperoxide ions.

Yet another object of the invention is to provide a method of deodorizing clothing with ozone so that it will not cause irritation or harm.

It is a further object of the invention to provide ozone in a compressed or generated form in a hand held container for application in the field by sportsmen.

Other objects and advantages of this invention will become apparent from the description of the preferred embodiments and the claims.

According to the present invention there is provided a method for the de-scenting of clothing used by sportsmen by the use of an oxidizing gas, namely, ozone or by ionization with UV light to produce hydroxyl and hydroperoxide ions. More particularly, the clothing of hunters can be treated with ozone or the hydroxyl and hydroperoxide ions either at home or in the field by the application of a small amount of ozone or the hydroxyl and hydroperoxide ions in order to remove the human scent or any other foreign scent. Also, the clothing of fishermen can be treated with the oxidizing gas while in the field to remove the odor of fish.

According to one embodiment of the invention, the human scent can be eliminated from clothing by applying a low volume stream of an oxidizing gas comprising ozone or hydroxyl and hydroperoxide ions directly on the hunter while he is wearing a hunting outfit. The gaseous stream is applied by an ozone generator which is hand held or a catalytic ionizer containing UV light and easily transported by the hunter. The gaseous stream can be applied directly to the clothing being worn by the hunter in an open atmosphere so as to be quickly diluted after it is passed over the clothing. Moreover, the gun or rifle or any other equipment, i.e. ammunition, arrows, scope, finders etc., of the hunter or sportsmen can be similarly treated to remove the gun or rifle or equipment odor.

In accordance with another embodiment of the invention, the clothing of the hunter can be treated before or after the hunt by placing the clothing in a container i.e. a sack, bag or box while passing the oxidizing gas into the container in order to remove any human or other scent foreign to that environment.

Another embodiment of the invention is that the instrument can be carried with the hunter or hung upwind of the body so it descents the human scent traveling downwind.

Also, some certain clothing is not cleaned after every use by the hunter or sportsmen such as gloves, hats, jackets, boots, and need to be deodorized and decontaminated before next use.

According to a further embodiment of the invention, the odor of fish can be eliminated from a fisherman's clothing, body or equipment by the direct application of a stream of ozone gas or hydroxyl and hydroperoxide ions to the site of the fish odor. Additionally, a fisherman's hands can be deodorized with ozone so as to remove the fish odor without causing irritation.

Each of the methods can be practiced in the open in the field of sports activity utilizing a low volume gas generator. The clothing is not decolorized as in applications involved in high volumes of ozone as found in the garment industry where ozone is used to both de-size and/or decolorize denim garments. The oxidizing gas may be used alone or diluted with air as when packaged in a compressed gas form. Ozone which is produced by generators in amounts up to 8000 mg/hr can be compressed or diluted with an inert gas and compressed into small containers.

It is understood that the term "sportsmen" is meant to include those individuals who may hunt with a camera or who merely enter an environment to observe animals in their habitat.

Additionally, the term "fishermen" includes those individuals who handle the fish caught by others.

Hydroxyl and hydroperoxide are produced in a process known as "Radiant Catalytic Ionization" which utilizes ultra violet light which activates a photocatalytic target.

Small ozone generators such as those producing 1 to 25 lbs. of ozone per day can be utilized. Also the ozone can be applied from compressed ozone-filled containers similar to compressed air.

Low volume ozone generators which generate up to 65 mg/hr of ozone and are portable as well as high volume ozone generators are currently sold by EcoQuest International of Greenville, Tenn. which also sells the generators of hydroxyl and hydroperoxide ions.

It will be appreciated by persons skilled in the art that numerous variations and/or modifications may be made to the invention without departing from the spirit or scope of the invention as broadly claimed.

What is claimed is:

1. A method of deodorizing a hunter, hunting clothing, and a hunting equipment while hunting, comprising:
   providing a portable oxidizing gas generator that has been transported to a field for discharging a stream of an oxidizing gas;
   positioning the portable oxidizing gas generator for use in the field where the hunter, the hunting clothing, the hunting equipment and game animals are present;
   applying the stream of oxidizing gas directly onto the hunter, the hunting clothing, and the hunting equipment in the field to deodorize the hunting clothing and the hunting equipment.

2. The method of claim 1 wherein the oxidizing gas comprises ozone.

3. The method of claim 1 wherein the oxidizing gas comprises hydroxyl and hydroperoxide.

4. The method of claim 1 wherein applying the stream of the oxidizing gas directly onto the hunting clothing and the hunting equipment occurs while the hunting clothing is being worn by the hunter.

5. The method of claim 1 wherein applying the stream of the oxidizing gas directly onto the hunting clothing and the hunting equipment occurs while the hunting equipment is not being held or carried by the hunter.

6. The method of claim 1 wherein applying the stream of the oxidizing gas descents a human scent traveling downwind toward the animals.

7. A method of eliminating scents from objects associated with hunting, comprising:
   providing a portable oxidizing gas generator that has been transported to a field for discharging a stream of an oxidizing gas;
   positioning the portable oxidizing gas generator for use in the field upwind of a hunting site wherein a hunter, a hunting equipment, and game animals are present;
   applying the stream of the oxidizing gas toward the scents from the hunter and the hunting equipment at the hunting site in the field to deodorize the objects so that air deodorized with respect to the scents from the hunter and the hunting equipment travels downwind of the hunter.

8. The method of claim 7 wherein the oxidizing gas generator produces 1 to 25 lbs. of the oxidizing gas per day.

9. The method of claim 7 wherein the oxidizing gas generator produces up to 65 mg/hr of the oxidizing gas.

10. The method of claim 7 wherein the oxidizing gas comprises ozone.

11. The method of claim 7 wherein the oxidizing gas comprises hydroxyl and hydroperoxide.

12. A method of eliminating scents, comprising:
    providing a portable ozone generator that has been transported to a field for discharging a stream of ozone;
    positioning the portable ozone generator for use in the field in which a hunter and game animals are present;
    applying the stream of ozone directly onto the hunter and equipment used by the hunter in the field to eliminate human scent and other scent foreign to the field such that air deodorized with respect to the human scent and the other scent foreign to the field travels downwind of the hunter.

13. The method of claim 12 wherein the ozone is diluted with air and packaged in a compressed gas form.

14. The method of claim 12 wherein the ozone generator produces 1 to 25 lbs. of ozone per day.

15. The method of claim 12 wherein the ozone generator produces up to 65 mg/hr of ozone.

16. The method of claim 12 wherein positioning the portable ozone generator includes positioning the portable ozone generator at least in part upwind of the hunter.

17. The method of claim 12 wherein positioning the portable ozone generator includes hanging the portable generator.

18. The method of claim 12 wherein positioning the portable ozone generator includes mounting the ozone generator on the hunter.

19. The method of claim 12 wherein applying the stream of ozone directly onto the hunter includes directing the stream of ozone to clothing being worn by the hunter.

20. The method of claim 12 wherein applying the stream of ozone directly onto the hunter includes directing the stream of ozone to the equipment of the hunter.

* * * * *